United States Patent [19]

Rissi et al.

[11] 4,248,877
[45] Feb. 3, 1981

[54] ORGANIC COMPOUNDS

[75] Inventors: Erwin Rissi, Basel; Anton Ebnöther, Arlesheim, both of Switzerland

[73] Assignee: Sandoz Ltd., Basel, Switzerland

[21] Appl. No.: 13,812

[22] Filed: Feb. 22, 1979

Related U.S. Application Data

[60] Division of Ser. No. 826,201, Aug. 19, 1977, which is a continuation-in-part of Ser. No. 650,105, Jan. 19, 1976, abandoned, which is a continuation-in-part of Ser. No. 479,850, May 14, 1974, abandoned.

[30] Foreign Application Priority Data

| Jun. 22, 1973 | [CH] | Switzerland | 9177/73 |
| Jun. 28, 1973 | [CH] | Switzerland | 9414/73 |
| Jun. 29, 1973 | [CH] | Switzerland | 9509/73 |
| Jul. 2, 1973 | [CH] | Switzerland | 9598/73 |
| Mar. 21, 1975 | [CH] | Switzerland | 3649/75 |
| Mar. 21, 1975 | [CH] | Switzerland | 3650/75 |
| Jan. 9, 1976 | [CH] | Switzerland | 215/76 |

[51] Int. Cl.³ .................. C07D 211/48; A61K 31/445
[52] U.S. Cl. ...................... 424/267; 546/221
[58] Field of Search .................. 546/221; 424/267

[56] References Cited

U.S. PATENT DOCUMENTS

| 3,438,991 | 4/1969 | Janssen et al. | 260/294.7 |
| 3,498,992 | 3/1970 | Kuhnis | 546/221 |
| 3,655,673 | 4/1972 | Maillard | 546/221 |

FOREIGN PATENT DOCUMENTS

| 2242387 | 3/1973 | Fed. Rep. of Germany . |
| 1534468 | 6/1968 | France . |
| 1186520 | 4/1970 | United Kingdom . |

OTHER PUBLICATIONS

Helv. Chim. Acta 130, (1958), pp. 1184–1190.
Maillard et al., Bull. Soc. Chim. France, (1970), pp. 1389–1394.
Chemical Abstracts, vol. 79, (1973), 5326b.
Chemical Abstracts, vol. 82, (1975), 156102p, abstracting OLS 2,429,373, 1/16/75.

*Primary Examiner*—Norma S. Milestone
*Attorney, Agent, or Firm*—Robert S. Honor

[57] ABSTRACT

The present invention concerns novel compounds of formula I,

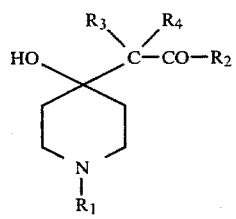

wherein
$R_1$ is phenethyl, phenethyl monosubstituted in the phenyl ring by fluorine, chlorine, bromine, lower alkyl or lower alkoxy, butyrophenone or butyrophenone monosubstituted in the phenyl ring by fluorine, chlorine, bromine, lower alkyl or lower alkoxy,
$R_2$ is an $OR_5$ group, wherein $R_5$ is lower alkyl, lower alkenyl, phenyl or phenyl monosubstituted by fluorine, chlorine, bromine, lower alkyl or lower alkoxy, or an

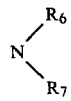

group, wherein independently each of $R_6$ and $R_7$ is hydrogen, lower alkyl or cycloalkylalkyl, cycloalkyl, phenyl, phenyl monosubstituted by fluorine, chlorine, bromine, lower alkyl or lower alkoxy, lower phenylalkyl or lower phenylalkyl monosubstituted in the phenyl ring by fluorine, chlorine, bromine, lower alkyl or lower alkoxy, or wherein $R_6$ and $R_7$ together with the nitrogen atom to which they are bound, form a saturated heterocycle of 5 to 6 ring members, which may optionally contain as second hetero atom oxygen, sulphur or nitrogen substituted by lower alkyl,
$R_3$ is lower alkyl or cycloalkylalkyl, cycloalkyl, phenyl or phenyl monosubstituted by fluorine, chlorine, bromine, lower alkyl or lower alkoxy, or when $R_1$ is phenethyl or phenethyl monosubstituted in the phenyl ring by fluorine, chlorine, bromine, lower alkyl or lower alkoxy, alternatively lower alkenyl, and
$R_4$ is hydrogen or lower alkyl, or
$R_3$ and $R_4$ together with the carbon atom to which they are bound form a cycloalkyl ring of 4 to 6 carbon atoms, and analgesic pharmaceutical compositions containing the compounds.

19 Claims, No Drawings

ORGANIC COMPOUNDS

This is a division, of application Ser. No. 826,201 filed Aug. 19, 1977, which in turn is a continuation-in-part of Ser. No. 650,105, filed Jan. 19, 1976, now abandoned, which in turn is a continuation-in-part of Ser. No. 479,850, filed May 14, 1974, now abandoned.

The present invention relates to new heterocyclic compounds.

In accordance with the invention there are provided new compounds of formula I,

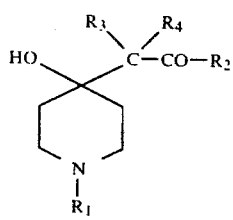

wherein
- $R_1$ is phenethyl, phenethyl monosubstituted in the phenyl ring by fluorine, chlorine, bromine, lower alkyl or lower alkoxy, butyrophenone or butyrophenone monosubstituted in the phenyl ring by fluorine, chlorine, bromine, lower alkyl or lower alkoxy,
- $R_2$ is an $OR_5$ group wherein $R_5$ is lower alkyl, lower alkenyl, phenyl or phenyl monosubstituted by fluorine, chlorine, bromine, lower alkyl or lower alkoxy, or an

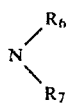

group, wherein independently each of $R_6$ and $R_7$ is hydrogen, lower alkyl or cycloalkylalkyl, cycloalkyl, phenyl, phenyl monosubstituted by fluorine, chlorine, bromine, lower alkyl or lower alkoxy, lower phenylalkyl or lower phenylalkyl monosubstituted in the phenyl ring by fluorine, chlorine, bromine, lower alkyl or lower alkoxy, or wherein $R_6$ and $R_7$ together with the nitrogen atom to which they are bound, form a saturated heterocycle of 5 to 6 ring members, which may optionally contain as second hetero atom oxygen, sulphur or nitrogen substituted by lower alkyl,
- $R_3$ is lower alkyl or cycloalkylalkyl, cycloalkyl, phenyl or phenyl monosubstituted by fluorine, chlorine, bromine, lower alkyl or lower alkoxy, or when $R_1$ is phenethyl or phenethyl monosubstituted in the phenyl ring by fluorine, chlorine, bromine, lower alkyl or lower alkoxy, alternatively lower alkenyl, and
- $R_4$ is hydrogen or lower alkyl, or
- $R_3$ and $R_4$ together with the carbon atom to which they are bound form a cycloalkyl ring of 4 to 6 carbon atoms.

Further, in accordance with the invention a compound of formula I may be obtained by a process comprising (a) reacting a compound of formula II,

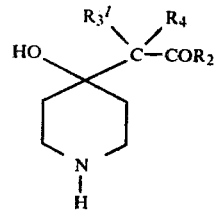

wherein
- $R_2$ and $R_4$ are as defined above, and
- $R_3{}^I$ is lower alkyl, cycloalkylalkyl, cycloalkyl, phenyl or phenyl monosubstituted by fluorine, chlorine, bromine, lower alkyl or lower alkoxy, or together with $R_4$ and the carbon atom to which they are bound form a cycloalkyl ring of 4 to 6 carbon atoms, with a compound of formula III, $$X-R_1 \qquad III$$

wherein
- $R_1$ is as defined above, and
- X is the acid radical of a reactive ester, to produce a compound of formula If,

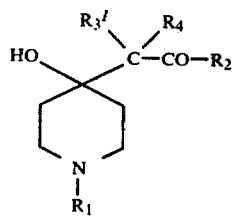

wherein $R_1$, $R_2$, $R_3{}^I$ and $R_4$ are as defined above, or (b) producing a compound of formula Ia,

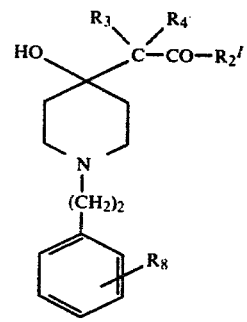

wherein
- $R_3$ and $R_4$ are as defined above,
- $R_2{}^I$ is an $OR_5$ group, wherein $R_5$ is as defined above, or an

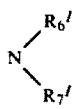

group, wherein
- $R_6{}^8$ is lower alkyl or cycloalkylalkyl, cycloalkyl, phenyl, phenyl monosubstituted by fluorine, chlorine, bromine, lower alkyl or lower alkoxy, lower phenylalkyl or lower phenylalkyl monosubstituted in the phenyl ring by fluorine, chlorine, bromine, lower alkyl or lower alkoxy, $R_7{}^I$ is hydrogen when $R_6{}^I$ and/or $R_3$ are phenyl or substituted phenyl, or $R_7{}^I$ is lower alkyl or cycloalkylalkyl, cycloalkyl, phenyl, phenyl monosubstituted by fluorine, chlorine, bromine, lower alkyl or lower alkoxy, lower phenylalkyl or lower phenylalkyl monosubstituted in the phenyl ring by fluorine, chlorine, bromine, lower alkyl or lower alkoxy, when $R_6{}^I$ is lower alkyl, cycloalkylalkyl or cycloalkyl, or $R_4$ is hydrogen and $R_6{}^I$ is phenyl or phenyl monosubstituted by fluorine, chlorine, bromine, lower alkyl or lower alkoxy, or $R_6{}^I$ and $R_7{}^I$ together with the nitrogen atom to which they are bound form a saturated heterocycle of 5 to 6 ring members, which may optionally contain as second hetero atom oxygen, sulphur, or nitrogen substituted by lower alkyl, and $R_8$ is fluorine, chlorine, bromine, lower alkyl or lower alkoxy, by reacting a compound of formula IV,

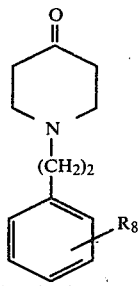

IV wherein $R_8$ is as defined above, with a compound of formula V,

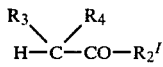

V wherein $R_3$, $R_4$ and $R_2{}^I$ are as defined above, or (c) producing a compound of formula Ib,

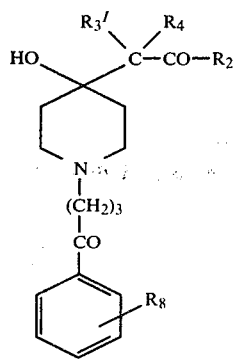

Ib wherein $R_2$, $R_3{}^I$, $R_4$ and $R_8$ are as defined above, by removing the protective group from a compound of formula VI,

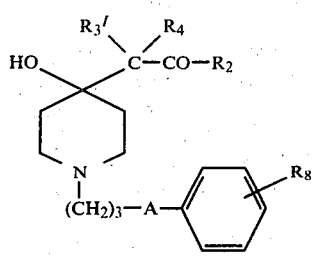

VI wherein $R_2$, $R_3{}^I$, $R_4$ and $R_8$ are as defined above, and

A is a carbonyl group protected by ketal formation, or (d) producing a compound of formula Ic,

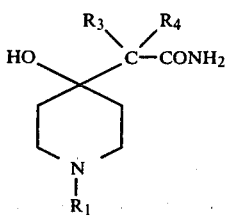

Ic wherein $R_1$, $R_3$ and $R_4$ are as defined above, by hydrolyzing the CN group to an $NH_2$—CO group in a compound of formula VII,

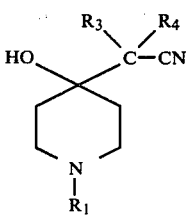

VII wherein $R_1$, $R_3$ and $R_4$ are as defined above, or (e) producing a compound of formula Id,

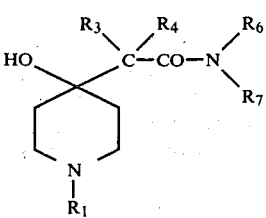

Id wherein $R_1$, $R_3$, $R_4$, $R_6$ and $R_7$ are as defined above, by reacting a compound of formula Ie,

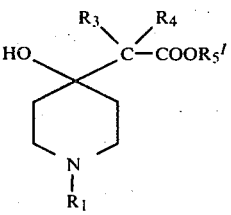

Ie wherein $R_1$, $R_3$ and $R_4$ are as defined above, and $R_5{}'$ is phenyl or phenyl monosubstituted by fluorine, chlorine, bromine, lower alkyl or lower alkoxy, with a compound of formula VIII,

   VIII wherein $R_6$ and $R_7$ are as defined above.

In the compounds of formula I $R_2$ preferably signifies an

group. The substituents $R_6$ and $R_7$ preferably denote lower alkyl groups or cycloalkyl groups. When $R_6$ and $R_7$ are lower alkyl groups, these preferably contain 1 to 4, especially 1 or 2 carbon atoms. When $R_6$ or $R_7$ contain cycloalkyl groups, these groups preferably contain 4 to 6 carbon atoms. $R_6$ preferably signifies lower alkyl, especially methyl, and $R_7$ preferably signifies cycloalkyl, especially cyclohexyl. When $R_6$ is hydrogen, $R_7$ preferably signifies a phenyl group or a substituted phenyl group. When $R_6$ or $R_7$ contain phenyl groups substituted by alkyl or alkoxy groups, these lower alkyl or alkoxy groups preferably contain 1 to 3 carbon atoms and especially signify methyl or methoxy. When $R_6$ and $R_7$ together with the nitrogen atom form a heterocycle, this preferably signifies the morpholine or N-methylpiperazine or piperidien ring.

When $R_2$ in the compounds of formula I is an $OR_5$ group, $R_5$ preferably signifies lower alkyl or alkenyl. When $R_5$ is lower alkyl, this preferably contains 1 to 4 carbon atoms and especially signifies methyl or ethyl. When $R_5$ is lower alkenyl, this preferably contains 3 to 5 carbon atoms and especially signifies the allyl group. When $R_5$ signifies phenyl substituted by a lower alkyl or alkoxy group, these groups preferably contain 1 to 3 carbon atoms and especially signify methyl or methoxy.

When $R_2$ in the compounds of formula I is an

group, $R_1$ preferably signifies a butyrophenone group or a substituted butyrophenone group. When $R_2$ is an $OR_5$ group, $R_1$ preferably signifies a phenethyl group or a substituted phenethyl group. When $R_1$ is a butyrophenone group, this is preferably substituted by fluorine, which is preferably in the p position, or is unsubstituted. When the butyrophenone group is substituted by lower alkyl or lower alkoxy, these groups preferably contain 1 to 3 carbon atoms and especially signify the methyl or the methoxy group. When each of $R_6$ and $R_7$ independently signifies lower phenylalkyl or lower phenylalkyl monosubstituted in the phenyl ring, the alkyl group preferably contains from 1 to 4 carbon atoms.

When $R_1$ is a phenethyl group, this is preferably substituted by chlorine, which is preferably in an o position, or is unsubstituted. When the phenethyl group is substituted by lower alkyl or lower alkoxy, these groups preferably contain 1 to 3 carbon atoms and especially signify the methyl or the methoxy group.

The substituent $R_3$ preferably signifies lower alkyl or alkenyl, and the substituent $R_4$ preferably signifies hydrogen. When $R_3$ is lower alkyl, this preferably contains 1 to 4 carbon atoms and especially signifies methyl or ethyl. When $R_3$ is lower alkenyl, this preferably contains 2 to 4 carbon atoms and especially signifies vinyl. When $R_3$ is a cycloalkyl group, this preferably contains 4 to 6 carbon atoms. When $R_3$ is phenyl substituted by lower alkyl or lower alkoxy, these groups preferably contain 1 to 3 carbon atoms and especially signify methyl or methoxy. When $R_3$ signifies cycloalkylalkyl this preferably signifies cycloalkyl (of 4 to 6 carbon atoms) alkyl (of 1 to 4 carbon atoms). When $R_4$ is lower alkyl, this preferably contains 1 to 3 carbon atoms and especially signifies methyl.

The preferred compounds are those wherein $R_1$ is a butyrophenone group or a butyrophenone group substituted by fluorine preferably in the p-position, $R_2$ is an

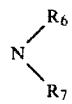

group, wherein $R_6$ is lower alkyl or cycloalkyl and $R_7$ is lower alkyl, or $R_6$ is hydrogen and $R_7$ is a phenyl group or a substituted phenyl group, or $R_2$ is an O-lower alkyl or an O-lower alkenyl group, and $R_3$ is lower alkyl and $R_4$ is hydrogen or lower alkyl. Specially suited compounds amongst these compounds containing a butyrophenone group are those wherein $R_2$ is a preferably disubstituted amine radical, especially the dimethylamine or the N-cyclohexyl-N-methylamine radical.

Compounds which are also suitable are those wherein $R_1$ is a phenethyl group or a phenethyl group substituted by chlorine preferably in the o position, $R_2$ is an $OR_5$ group, wherein $R_5$ is lower alkyl, preferably methyl or ethyl, or lower alkenyl, or $R_2$ is an

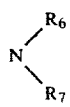

group, wherein $R_6$ is lower alkyl or cycloalkyl and $R_7$ is lower alkyl, or $R_6$ is phenyl or substituted phenyl and $R_7$ is hydrogen, and $R_3$ is lower alkyl or alkenyl and $R_4$ is lower alkyl or hydrogen. Especially suited amongst these compounds containing a phenethyl group are those wherein $R_2$ is an O-alkyl or O-alkenyl, especially the methoxy, ethoxy or allyloxy group. When

signifies a saturated heterocycle, this may, for example, be pyrollidino, alkylpiperazino, morpholino, thiomorpholino and piperidino. Any carbon-containing radical not particularly defined herein preferably contains up to 4 carbon atoms.

The reaction of a compound of formula II with a compound of formula III in accordance with process variant (a) is preferably effected in an inert organic solvent, if desired with the addition of an acid-binding agent or in the presence of an excess of the compound of formula II used. Examples of inert solvents which may be used are, for example, aromatic hydrocarbons such as benzene, toluene or xylene, chlorinated hydrocarbons such as chloroform or carbon tetrachloride, or a lower alcohol such as ethanol, or DMF or DMA. Examples of acid-binding agents which may be used are alkali metal carbonates such as potassium carbonate or sodium carbonate, or tertiary amines such as triethylamine or pyridine. It is preferred to use compounds of formula III wherein X is chlorine, bromine, iodine or the radical of an organic sulphonic acid, for example an alkylsulphonyloxy or an arylsulphonyloxy radical. The reaction is preferably effected at a temperature between room temperature and approximately 100° C.

The addition of an ester or an amide of formula V on a 4-piperidone derivative of formula IV in accordance with process variant (b) may, for example, be effected in the presence of a strong basic condensation agent. Examples of inert anhydrous solvents which may be used are saturated hydrocarbons such as hexane, ethers such as diethyl ether or tetrahydrofuran, or aromatic hydrocarbons such as benzene or toluene. Especially suited is, for example, a mixture of hexane/tetrahydrofuran. When the CO—$R_2^I$ group in the compounds of formula V is an ester group or a tertiary amide group, suitable basic condensation agents are alkali metal amides such as lithium or sodium amide, it being preferred to use organic lithium amides, especially diisopropyl lithium amide, cyclohexylmethyl lithium amide or cyclohexylisopropyl lithium amide, and the reaction may be effected at low temperatures, preferably at a temperature between $-75°$ and $-20°$ C. If desired, a catalytic amount of an organic peroxide or of dimethyl sulphoxide may be added in order to accelerate the reaction when using lithium or sodium amide. When the CO—$R_2^I$ group is a secondary phenylamide group or a substituted secondary phenylamide group, the addition may be effected in the presence of a very strong basic condensation agent capable of forming a dianion of formula Va,

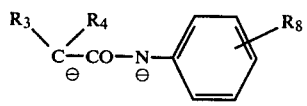

wherein $R_3$, $R_4$ and $R_8$ are as defined above, from an amide of formula Vb,

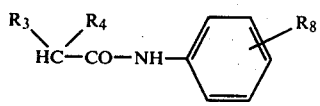

wherein $R_3$, $R_4$ and $R_8$ are as defined above. Examples of suitable compounds therefor are lower alkyl alkali metal compounds, preferably lower alkyl lithium compounds, especially n-butyl lithium or methyl lithium, or also phenyl lithium or organic Grignard compounds, e.g. alkyl magnesium halides. The reaction temperature may be between about 0° and 50° C.

The removal of the protective groups from ketals of formula VI in accordance with process variant (c) may be effected in known manner. Examples of suitable protective groups of the carbonyl function are optionally mixed ketals of lower 1- or 2-valent alcohols. It is preferred to use cyclic ketals with 5 or 6 ring members, especially dioxolane. The ketal splitting may be effected on crude ketals of formula VI, for example by hydrolysis in an acid medium, e.g. with a dilute mineral acid, e.g. with approximately 2 N hydrochloric acid, preferably at a temperature between about 0° and 25° C. When the CO—$R_2$ group in the compounds of formula VI is an ester group, the reaction conditions for the ketal splitting must be so mild that a simultaneous ester splitting is avoided.

The production of compounds of formula Ic in accordance with process variant (d) may be effected in accordance with the usual methods for the hydrolysis of cyanides. The compounds of formula VII may, for example, be reacted with water, optionally with the addition of a further inert organic solvent, preferably miscible with water, e.g. a lower alcohol, acetone or dioxane, preferably in the presence of a basic catalyst. The hydrolysis is preferably effected in an alkaline medium, e.g. in the presence of dilute alkali metal hydroxide solutions, e.g. dilute caustic soda solution. In accordance with a preferred method of the process the compounds of formula VII are converted into amides of formula Ic in the presence of a lower alcohol and a dilute, e.g. a 1 N to 5 N caustic soda solution, with a hydrogen peroxide solution at a slightly elevated temperature, e.g. at a temperature between about 20° and 50° C. Any N-oxides which may result as by-products may be reduced to compounds of formula Ic by subsequent treatment of the crude reaction product with sodium disulphite solution in an aqueous medium at a low temperature, preferably at a temperature between about 0° and 20° C.

The formation of amides of formula Id from the phenyl esters of formula Ie may be effected in known manner by reacting the esters of formula Ie with preferably an excess of an amine of formula VIII, e.g. at an elevated temperature, preferably at a temperature between about 50° and 150° C. When amines having a low boiling point are used, the reaction may preferably be effected in an autoclave under pressure. If desired, an inert organic solvent may be added to the reaction mixture. Examples of suitable solvents are aromatic hydrocarbons such as benzene or xylene, cyclic ethers such as dioxane or tetrahydrofuran, dimethyl formamide or dimethyl acetamide.

The compounds of formula I may be isolated from the reaction mixture and purified in known manner. Free base forms of the compounds may be converted into acid addition salt forms in known manner, and vice versa.

Suitable inorganic acids for salt formation include hydrochloric acid and hydrobromic acid and suitable organic acids include fumaric acid, maleic acid and napthalene 1,5-disulphonic acid.

The starting materials may be obtained as follows:

(a') Compounds of formula II may, for example, be obtained by debenzylating in known manner a compound of formula IX;

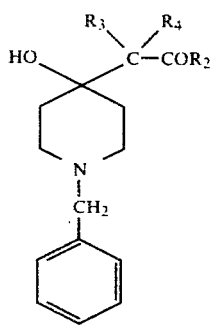

wherein $R_2$, $R_3$ and $R_4$ are as defined above. The removal of the benzyl group may, for example, be effected by catalytic hydrogenation, whereby any double bonds which may be present in the radicals $R_3$ or $R_2$ are likewise hydrogenated.

(b') Compounds of formula II wherein $R_2$ is an O-alkenyl group, are preferably obtained by an interchange of ester radicals in a corresponding alkyl ester ($R_2$=an O-alkyl group) with an alkenol in known manner.

(c') Amides of formula IIa,

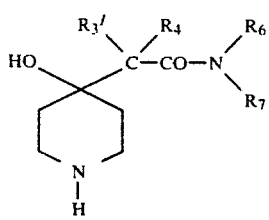

wherein $R_3'$, $R_4$, $R_6$ and $R_7$ are as defined above, may, for example, also be obtained by reacting a corresponding phenyl ester of formula II ($R_2$=O-phenyl) with a compound of formula VIII, for example under the reaction conditions described in process variant (e).

(d') Compounds of formula VI may, for example, be obtained by reacting a compound of formula II with a compound of formula X,

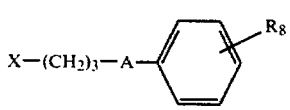

wherein $R_8$, A and X are as defined above. The reaction may, for example, be effected under the reaction conditions described in process variant (a).

(e') Compounds of formula VIIa,

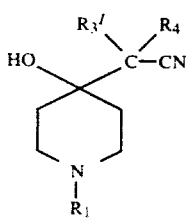

wherein $R_1$, $R_3'$ and $R_4$ are as defined above, may, for example, be obtained by reacting a compound of formula XI,

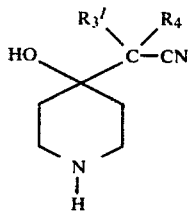

wherein $R_3'$ and $R_4$ are as defined above, with a compound of formula III or a compound of formula X, for example under the reaction conditions described in process variant (a), and any ketal protective groups which may be present are subsequently removed.

(f') Compounds of formula VIIa,

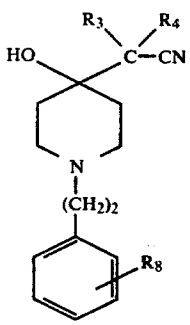

wherein $R_3$, $R_4$ and $R_8$ are as defined above, may, for example, be obtained by reacting a compound of formula IV with a compound of formula XII,

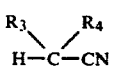

wherein $R_3$ and $R_4$ are as defined above, for example under the reaction conditions described in process variant (b).

(g') Compounds of formula IXa,

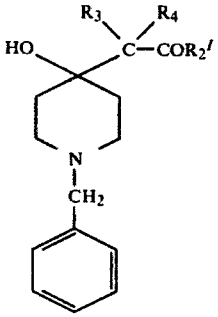

wherein $R_2'$, $R_3$ and $R_4$ are as defined above, may, for example, be obtained by reacting N-benzylpiperidone with a compound of formula V, for example under the reaction conditions described in process variant (b).

(h') Compounds of formula IXb,

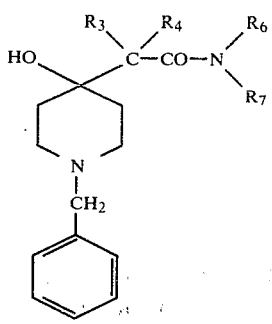

wherein $R_3$, $R_4$, $R_6$ and $R_7$ are as defined above, may, for example, also be obtained by reacting a corresponding phenyl ester of formula IXa ($R_2{}^I$=O-phenyl) with a compound of formula VIII, for example under the reaction conditions described in process variant (e).

(i') Compounds of formula IXb wherein $R_6$ and $R_7$ are hydrogen, may, for example, also be obtained by hydrolysis of a nitrile of formula XIII,

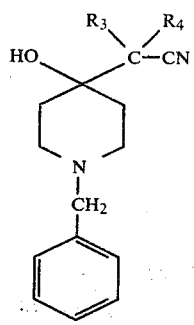

wherein $R_3$ and $R_4$ are as defined above, for example under the reaction conditions described in process variant (d).

(j') Compounds of formula XI may, for example, be obtained by reacting N-benzyl-4-piperidone with a compound of formula XII, for example under the reaction conditions described in process variant (b), and the resulting compounds of formula XIII may subsequently be debenzylated, for example by catalytic hydrogenation in a manner analogous to that described in process variant (a').

Insofar as the production of the starting materials is not described, these are known or may be produced in accordance with known processes, or in a manner analogous to the processes described herein or to known processes.

In the following non-limitative Examples all temperatures are indicated in degrees Centigrade.

EXAMPLE 1:
2-[4-hydroxy-1-(4-oxo-4-phenylbutyl)-4-piperidyl]propionic acid ethyl ester [process variant (a)]

A solution of 8.6 g of 4-chlorobutyrophenone in 30 cc of N,N-dimethyl formamide is added dropwise at 60° C., with stirring, to a solution of 18.9 g of crude 2-(4-hydroxy-4-piperidyl)propionic acid ethyl ester in 250 cc of N,N-dimethyl formamide. The reaction mixture is allowed to react at 60° for 7½ hours, the solvent is removed by evaporation at reduced pressure and the resulting residue is taken up in chloroform. The chloroform solution is repeatedly extracted with water, dried over magnesium sulphate and evaporated to dryness. The resulting residue is dissolved in ethanol, hydrochloric acid in ethanol is added and subsequently ether is added until the reaction solution is turbid, and the resulting crude crystalline product is purified by repeated crystallization from ethanol/ether. The hydrochloride form of the title compound, having a M.P. of 130°–132°, is obtained.

The 2-(4-hydroxy-4-piperidyl)propionic acid ethyl ester, used as starting material, is produced as follows:

(a) A solution of 23 cc of propionic acid ethyl ester in 100 cc of anhydrous tetrahydrofuran is added dropwise at −75° to a solution of N,N-diisopropyllithium amide (produced from 56.7 cc of N,N-diisopropylamine in 300 cc of anhydrous tetrahydrofuran and 160 cc of a 20% n-butyl-lithium solution in hexane at a temperature of −75°). The reaction mixture is stirred at the same temperature for one hour and a solution of 37.8 g of 1-benzyl-4-piperidone in 100 cc of anhydrous tetrahydrofuran is subsequently added dropwise at −75°. After allowing to react at the same temperature for one hour, the reaction mixture is allowed to warm to about −10° and is decomposed with 200 cc of a 20% potassium carbonate solution. Extraction is repeatedly effected with ether, the extracts are dried over magnesium sulphate and evaporated to dryness. The resulting 2-(1-benzyl-4-hydroxy-4-piperidyl)propionic acid ethyl ester is used as crude product for the next reaction.

(b) A solution of 57.1 g of 2-(1-benzyl-4-hydroxy-4-piperidyl)propionic acid ethyl ester in 580 cc of glacial acetic acid is hydrogenated in the presence of 5.7 g of a palladium catalyst (10% on charcoal) at a temperature of 70° and a pressure of 21 atmospheres in a 1-liter autoclave. After the calculated amount of hydrogen has been taken up, the reaction mixture is filtered and evaporated to dryness. The residue is dissolved in 600 cc of chloroform and a paste of 216 g of potassium carbonate and 100 cc of water is added to this solution while cooling with ice and stirring. The chloroform solution is decanted, the mash remaining in the reaction vessel is washed with chloroform and the chloroform phases which have been dried over magnesium sulphate are concentrated by evaporation. The resulting 2-(4-hydroxy-4-piperidyl)propionic acid ethyl ester is used as crude product for the next reaction.

EXAMPLE 2:
2-[1-(4-p-fluorophenyl-4-oxobutyl)-4-hydroxy-4-piperidyl]propionic acid ethyl ester [process variant (c)]

20.5 g of crude 2-{1-[4-(2,2-ethylenedioxy)-4-(p-fluorophenyl)-butyl]-4-hydroxy-4-piperidyl}-propionic acid ethyl ester are taken up in 750 cc of chloroform, 300 cc of 2 normal hydrochloric acid are added to the solution and this is stirred at room temperature for 11 hours. The chloroform phase is separated, dried over magnesium sulphate and concentrated by evaporation. The free base is recrystallized from ethanol with the addition of ether and is then converted into the hydrochloride. This has a M.P. of 183°–185°.

The starting material may be obtained as follows:

(a) 10.2 g of sodium carbonate are added to a solution of 9.7 g of crude 2-(4-hydroxy-4-piperidyl)propionic acid ethyl ester in 100 cc of dimethyl formamide and the mixture is heated to 100°. 13.0 g of 2-(3-chloropropyl)-2-(p-fluorophenyl)-1,3-dioxolane in 25 cc of dimethyl formamide are then added dropwise within 15 minutes and stirring is subsequently effected at 100° for 5 hours. The dimethyl formamide is removed by evaporation at reduced pressure, the resulting compound is used for the next reaction without purification.

The following compounds may also be obtained in a manner analogous to Example 1 or 2, by reaction of the corresponding (4-hydroxy-4-piperidyl)carboxylic acid esters, produced in a manner analogous to Example 1 (a) and (b), with the corresponding 4-chlorobutyrophenone derivatives or by splitting the corresponding 2-phenyl-2-[3-(4-hydroxypiperidyl)propyl]-1,3-dioxolane derivatives produced in a manner analogous to Example 2(a):

2-(4-hydroxy-4-piperidyl)propionic acid ethyl ester and 11.5 g of potassium carbonate in 150 cc of dimethyl formamide. The reaction mixture is stirred at 60° for a further 1½ hours, is then poured in a 10% potassium carbonate solution containing ice and extraction is effected with ether. The title compound, obtained after drying the ether extracts over magnesium sulphate and concentrating by evaporation, is dissolved in acetone, the calculated amount of maleic acid is added, and the resulting crude hydrogen maleate is repeatedly recrystallized from acetone. The hydrogen maleate form of

| Compound | Observations, physical constants |
| --- | --- |
| 2-[4-hydroxy-1-(4-oxo-4-phenylbutyl)-4-piperidyl]-butyric acid ethyl ester | M.P. of the hydrochloride form: 152°-154° (from ethanol) |
| 2-[4-hydroxy-1-(4-oxo-4-phenylbutyl)-4-piperidyl]-2-cyclohexyl-acetic acid ethyl ester | M.P. of the hydrobromide form: 142°-144° (from ethanol/ether) |
| 2-[1-(4-p-fluorophenyl-4-oxobutyl)-4-hydroxy-4-piperidyl]-propionic acid ethyl ester | M.P. of the hydrochloride form: 183°-185° (from acetone) |
| 2-[4-hydroxy-1-(4-oxo-4-phenylbutyl)-4-piperidyl]-isobutyric acid ethyl ester | M.P. of the neutral naphthalene-1,5-disulphonate form: 238°-239.5° (from ethanol or methanol) |
| 1-[4-hydroxy-1-(4-oxo-4-phenylbutyl)-4-piperidyl]-1-cyclopentane-carboxylic acid ethyl ester | M.P. of the hydrochloride form: 154°-156° (from acetone) |
| 1-[4-hydroxy-1-(4-oxo-4-phenylbutyl)-4-piperidyl]-1-cyclohexane-carboxylic acid ethyl ester | M.P. of the hydrochloride form: 179°-181° (from ethanol/acetone) |
| 2-cyclopentyl-2-[4-hydroxy-1-(4-oxo-4-phenylbutyl)-4-piperidyl]acetic acid ethyl ester | M.P. of the hydrobromide form: 136.5°-138° (from ethanol/ether) |
| 2-[4-hydroxy-1-(4-oxo-4-phenylbutyl)-4-piperidyl]-3-cyclopentyl-propionic acid ethyl ester | M.P. of the hydrogen fumarate form: 134°-136° (from acetone) |
| 2-[4-hydroxy-1-(4-oxo-4-phenylbutyl)-4-piperidyl]-3-cyclohexyl-propionic acid ethyl ester | M.P. of the hydrobromide form: 150°-151.5° (from ethanol/ether) |
| 2-[4-hydroxy-(4-oxo-4-phenylbutyl)-4-piperidyl]-propionic acid tert.butyl ester | M.P. of the hydrogen maleate form: 135°-136° |
| 2-[1-(4-p-fluorophenyl-4-oxobutyl)-4-hydroxy-4-piperidyl]-isobutyric acid ethyl ester | M.P. of the maleate form: 99°-100° (from acetone/ether) |
| 2-[1-(4-p-fluorophenyl-4-oxobutyl)-4-hydroxy-4-piperidyl]-isobutyric acid methyl ester | M.P. of the maleate form: 80°-82° (from acetone/ether) |
| 2-[4-hydroxy-1-(4-oxo-4-phenylbutyl)-4-piperidyl]-propionic acid o-tolyl ester | |
| 2-[4-hydroxy-1-(4-oxo-4-m-tolylbutyl)-4-piperidyl]-isobutyric acid ethyl ester | |
| 2-[4-hydroxy-1-(4-p-methoxyphenyl-4-oxobutyl)-4-piperidyl]propionic acid ethyl ester | |
| 2-[1-(4-p-chlorophenyl-4-oxobutyl)-4-hydroxy-4-piperidyl]-2-phenylacetic acid ethyl ester | |
| 2-[1-(4-p-fluorophenyl-4-oxobutyl)-4-hydroxy-4-piperidyl]isobutyric acid allyl ester | |
| 2-[4-hydroxy-1-(4-oxo-4-phenylbutyl)-4-piperidyl]-propionic acid phenyl ester | |
| 2-[1-(4-p-fluorophenyl-4-oxobutyl)-4-hydroxy-4-piperidyl]-propionic acid m-methoxyphenyl ester | |
| 2-[1-(4-p-fluorophenyl-4-oxobutyl)-4-hydroxy-4-piperidyl]-butyric acid p-chlorophenyl ester | |
| 2-[4-hydroxy-1-(4-oxo-4-phenylbutyl)-4-piperidyl]-2-p-chlorophenylacetic acid ethyl ester | |
| 2-[4-hydroxy-1-(4-oxo-4-phenylbutyl)-4-piperidyl]-2-phenylacetic acid ethyl ester | |
| 2-[1-(4-p-fluorophenyl-4-oxobutyl)-4-hydroxy-4-piperidyl]-2-m-tolyl-acetic acid ethyl ester | |
| 2-[1-(4-p-fluorophenyl-4-oxobutyl)-4-hydroxy-4-piperidyl]-2-p-methoxyphenylacetic acid ethyl ester | |

EXAMPLE 3:
2-(4-hydroxy-4-piperidyl-1-phenethyl-4-piperidyl)propionic acid ethyl ester [process variant (a)]

A solution of 12.0 g of phenethyl bromide in 50 cc of dimethyl formamide is added dropwise at a temperature of 60°, with stirring, to a suspension of 18.9 g of crude the title compound has a M.P. of 138°-139°.

The following compounds may be obtained in a manner analogous to Example 3, by reaction of the corresponding (4-hydroxy-4-piperidyl)carboxylic acid esters produced in a manner analogous to Example 1 (a) and (b), with the corresponding β-halogen-phenethyl derivatives:

| Compound | Observations, physical constants |
| --- | --- |
| 2-(1-o-chlorophenethyl-4-hydroxy-4-piperidyl)-propionic acid ethyl ester | M.P. of the hydrogen fumarate form: 132°-134° (from ethanol) |
| 2-(4-hydroxy-1-phenethyl-4-piperidyl)-2-cyclohexyl-acetic acid ethyl ester | M.P. of the neutral fumarate form: 161°-163° (from ethanol/ether) |

-continued

| Compound | Observations, physical constants |
|---|---|
| 2-(1-o-chlorophenethyl-4-hydroxy-4-piperidyl)-2-cyclohexyl-acetic acid ethyl ester | M.P. of the hydrogen fumarate form: 172.5°–174° (from ethanol) |
| 2-(1-o-chlorophenethyl-4-hydroxy-4-piperidyl)-propionic acid isopropyl ester | M.P. of the hydrogen fumarate form: 138°–139° (from acetone) |
| 2-(1-o-chlorophenethyl-4-hydroxy-4-piperidyl)-propionic acid tert.butyl ester | M.P. of the hydrogen fumarate form: 151°–152° (from ethanol/ether) |
| 2-(1-o-chlorophenethyl-4-hydroxy-4-piperidyl)-2-phenylacetic acid ethyl ester | M.P. 93°–96° (from ether/petroleum ether) |
| 2-(1-o-chlorophenethyl-4-hydroxy-4-piperidyl)-2-p-chlorophenylacetic acid ethyl ester | |
| 2-(1-o-chlorophenethyl-4-hydroxy-4-piperidyl)-propionic acid phenyl ester | M.P. (HCl salt) 177°–178° (from acetone) |
| 2-(1-o-chlorophenethyl-4-hydroxy-4-piperidyl)-propionic acid methyl ester | M.P. (hydrogen maleate salt) 122°–123° (from acetone/ether) |
| 2-(1-o-chlorophenethyl-4-hydroxy-4-piperidyl)-isobutyric acid ethyl ester | M.P. of the hydrogen maleate form: 147°–148° (from acetone/ether) |
| 2-(1-o-chlorophenethyl-4-hydroxy-4-piperidyl)-propionic acid allyl ester | M.P. of the hydrogen maleate form: 96°–99° (from acetone) |
| 2-(4-hydroxy-1-o-methoxyphenethyl-4-piperidyl)-propionic acid ethyl ester | |
| 2-(4-hydroxy-1-m-methylphenethyl-4-piperidyl)-propionic acid ethyl ester | |
| 2-(1-p-fluorophenethyl-4-hydroxy-4-piperidyl)-propionic acid ethyl ester | |
| 2-(1-o-chlorophenethyl-4-hydroxy-4-piperidyl)-2-p-fluorophenylacetic acid ethyl ester | |
| 2-(1-o-chlorophenethyl-4-hydroxy-4-piperidyl)-2-m-methoxyphenylacetic acid ethyl ester | |
| 2-(1-o-chlorophenethyl-4-hydroxy-4-piperidyl)-2-p-tolyl-acetic acid ethyl ester | |
| 2-(1-o-chlorophenethyl-4-hydroxy-4-piperidyl)-propionic acid p-chlorophenyl ester | |
| 2-(1-o-chlorophenethyl-4-hydroxy-4-piperidyl)-propionic acid o-tolyl ester | |
| 2-(1-o-chlorophenethyl-4-hydroxy-4-piperidyl)-propionic acid p-fluorophenyl ester | |
| 1-(1-o-chlorophenethyl-4-hydroxy-4-piperidyl)-1-cyclohexane-carboxylic acid ethyl ester | |
| 2-(1-o-chlorophenethyl-4-hydroxy-4-piperidyl)-isobutyric acid allyl ester | M.P. (hydrogen maleate) 100°–102° (from acetone) |

EXAMPLE 4:
2-[4-hydroxy-1-(4-oxo-4-phenylbutyl)-4-piperidyl]-N,N-dimethyl propionamide [process variant (a)]

A solution of 18.1 g of 4-chlorobutyrophenone in 30 cc of N,N-dimethyl formamide is added dropwise at 60°, with stirring, to a solution of 39.6 g of 2-(4-hydroxy-4-piperidyl)propionic acid N,N-dimethylamide in 150 cc of N,N-dimethyl formamide. The mixture is allowed to react at 60° for 6 hours, the solvent is removed by evaporation at reduced pressure and the resulting residue is taken up in chloroform. The chloroform solution is repeatedly extracted with water, is dried over magnesium sulphate and evaporated to dryness. The resulting residue is dissolved in ethanol, the calculated amount of fumaric acid is added to the solution and ether is subsequently added until the solution becomes turbid. Purification is effected by recrystallizing the crude hydrogen fumarate repeatedly from ethanol/ether. The hydrogen fumarate form of the title compound, having a M.P. of 155°–157°, is obtained.

The starting material is obtained as follows:

(a) A solution of 20.2 g of propionic acid N,N-dimethylamide in 75 cc of anhydrous tetrahydrofuran is added dropwise at −75° to a solution of N,N-diisopropyl-lithium amide (produced from 35 g of diisopropylamine in 200 cc of anhydrous tetrahydrofuran and 100 cc of a 20% n-butyl-lithium solution in hexane at a temperature of −75°). After stirring at the same temperature for one hour, a solution of 37.8 g of 1-benzyl-4-piperidone in 150 cc of tetrahydrofuran is added within 20 minutes and the mixture is allowed to react for 2 hours at about −70°. The reaction temperature is then allowed to rise to about −10° and the reaction mixture is decomposed with 300 cc of a 20% potassium carbonate solution. After extracting repeatedly with ether, the crude product is isolated by drying the extracts over magnesium sulphate and concentratrating by evaporation. The resulting crude 2-(1-benzyl-4-hydroxy-4-piperidyl)propionic acid N,N-dimethylamide is used for the next reaction without purification.

(b) 57.7 g of 2-(1-benzyl-4-hydroxy-4-piperidyl)propionic acid N,N-dimethylamide in 1000 cc of glacial acetic acid are hydrogenated at 70° and a pressure of 21 atmospheres, in the presence of 5.8 g of a palladium catalyst (10% on charcoal). After the take up of the calculated amount of hydrogen, the reaction mixture is filtered and evaporated to dryness. The residue is dissolved in 600 cc of chloroform and a paste of 216 g of potassium carbonate and 100 cc of water is added to this solution while cooling with ice and stirring. The chloroform solution is decanted, the mash remaining in the reaction vessel is washed with chloroform and the chloroform phases which have been dried over magnesium sulphate are concentrated by evaporation. The resulting 2-(4-hydroxy-4-piperidyl)propionic acid N,N-dimethylamide is used as crude product for the next reaction.

EXAMPLE 5:
2-[1-(4-p-fluorophenyl-4-oxobutyl)-4-hydroxy-4-piperidyl]-N-phenylpropionamide [process variant (c)]

21.5 g of crude 2-{1-[4-(2,2-ethylenedioxy)-4-p-fluorophenylbutyl]-4-hydroxy-4-piperidyl}-N-phenylpropionamide are taken up in 750 cc of chloroform and stirring is effected at 25° for 10 hours with the addition of 400 cc of 2 N hydrochloric acid. The organic phase is separated and concentrated by evaporation at reduced pressure and the residue is taken up in 2 N hydrochloric acid. The acid aqueous solution is extracted twice with ether, is rendered alkaline with a 2 N caustic soda solution while cooling with ice and the resulting title compound is extracted with ether. The resulting crude product is dissolved in acetone, an equivalent amount of maleic acid is added, and after the addition of ether crystallizes as maleate. M.P. of the maleate form of the title compound: 111°–113°.

The starting material may be obtained as follows:

(a) 48 cc of n-butyl-lithium are added dropwise at 0°, in an atmosphere of nitrogen and with stirring, to a solution of 9 g of N-phenylpropionamide in 90 cc of anhydrous tetrahydrofuran. The mixture is stirred for a further 2½ hours at 45°–48° and a solution of 7.9 g of N-benzyl-4-piperidone in 25 cc of anhydrous tetrahydrofuran is added dropwise within 50 minutes. The heating (oil bath) is removed and the reaction mixture is stirred for a further hour while cooling slowly. The reaction solution is then decomposed with 10 cc of a 20% potassium carbonate solution while stirring and cooling with ice, dilution is effected with ether and the organic phase is decanted, dried over magnesium sulphate and concentrated by evaporation at reduced pressure. The resulting crude 2-(1-benzyl-4-hydroxy-4-piperidyl)-N-phenylpropionamide is purified over silica gel (eluant: chloroform containing 3% of methanol) and after concentrating the solution in ethanol, an equivalent amount of fumaric acid is added thereto, whereby the product crystallizes as fumarate. M.P. 228°–239°.

(b) A solution of 16.0 g of 2-(1-benzyl-4-hydroxy-4-piperidyl)-N-phenylpropionamide in 160 cc of glacial acetic acid is hydrogenated at a temperature of 50° and a pressure of 31 atmospheres for 15 hours in the presence of 1.6 g of a palladium catalyst (10% on charcoal). The reaction mixture is worked up in a manner analogous to that described in Example 4(b) and the resulting 2-(4-hydroxy-4-piperidyl)-N-phenylpropionamide is used as crude product for the next reaction.

(c) 11.0 g of potassium carbonate are added to a solution of 11.0 g of crude 2-(4-hydroxy-4-piperidyl)-N-phenylpropionamide in 150 cc of dimethyl acetamide and the mixture is heated to 100° while stirring. A solution of 13.1 g of 2-(3-chloropropyl)-2-(p-fluorophenyl)-1,3-dioxolane in 20 cc of dimethyl acetamide is subsequently added dropwise while stirring vigorously and the temperature is kept at 100° for 4 hours. The solution is subsequently cooled and the potassium carbonate is filtered off and the filtrate concentrated by evaporation at reduced pressure. The resulting compound is used for the next reaction without purification.

The following compounds may be obtained in a manner analogous to that described in Example 4 or 5, by reacting the corresponding (4-hydroxy-4-piperidyl)carboxylic acid amides, produced in a manner analogous to Example 4(a) and (b), with the corresponding 4-chlorobutyrophenone derivatives, or by splitting the corresponding 2-phenyl-2-[3-(4-hydroxypiperidyl)-propyl]-1,3-dioxolane derivatives produced in a manner analogous to Example 5(a) to (c):

| Compound | Observations, physical constants |
| --- | --- |
| 2-[4-hydroxy-1-(4-oxo-4-phenylbutyl)-4-piperidyl]-N-cyclohexyl-N-methyl propionamide | M.P. of the hydrobromide form: 190°–191.5° (from isopropanol) |
| 2-[1-(4-fluorophenyl-4-oxobutyl)-4-hydroxy-4-piperidyl]-N,N-dimethyl propionamide | M.P. of the hydrochloride form: 200°–202° (from ethanol/ether) |
| 2-[4-hydroxy-1-(4-oxo-4-phenylbutyl)-4-piperidyl]-N-methyl-N-phenyl propionamide | M.P. of the hydrogen fumarate form: 203°–204° (from ethanol) |
| 2-[1-(4-p-fluorophenyl-4-oxobutyl)-4-hydroxy-4-piperidyl]-N-methyl-N-phenyl propionamide | M.P. of the hydrogen maleate form: 146°–148° |
| 2-[1-(4-p-fluorophenyl-4-oxobutyl)-4-hydroxy-4-piperidyl]-N,N-dimethylisobutyric acid amide | M.P. of the hydrochloride form: 215°–216° (from ethanol) |
| 1-{2-[4-hydroxy-1-(4-oxo-4-phenylbutyl)-4-piperidyl]-2-methylpropionyl}pyrrolidine | M.P. of the hydrochloride form: 192°–194° (from acetone) |
| 2-[4-hydroxy-1-(4-oxo-4-phenylbutyl)-4-piperidyl]-N-isopropyl-N-methyl isobutyric acid amide | |
| N-cyclohexyl-2-[4-hydroxy-1-(4-oxo-4-phenylbutyl)-4-piperidyl]-N-isopropyl-propionamide | |
| 2-[4-hydroxy-1-(4-oxo-4-o-tolylbutyl)-4-piperidyl]-N-p-chlorophenyl-N-methyl propionamide | |
| 2-[4-hydroxy-1-(4-oxo-4-phenylbutyl)-4-piperidyl]-N-cyclohexyl-N-methyl-2-phenylacetamide | |
| 2-[1-(4-p-fluorophenyl-4-oxobutyl)-4-hydroxy-4-piperidyl]-N-p-fluorophenyl-N-methyl propionamide | |
| 2-[1-(4-p-fluorophenyl-4-oxobutyl)-4-hydroxy-4-piperidyl]-N-m-methoxyphenyl propionamide | |
| 2-[1-(4-p-fluorophenyl-4-oxobutyl)-4-hydroxy-4-piperidyl]-2-p-chlorophenyl-N-o-tolyl-acetamide | |
| 2-[1-(4-p-fluorophenyl-4-oxobutyl)-4-hydroxy-4-piperidyl]-propionamide | |
| 2-[4-hydroxy-1-(4-oxo-4-phenylbutyl)-4-piperidyl]-propionamide | |
| 2-[4-hydroxy-1-(4-oxo-4-phenylbutyl)-4-piperidyl]-2-phenylacetamide | |
| 2-cyclohexyl-2-[1-(4-p-fluorophenyl-4-oxobutyl)-4-hydroxy-4-piperidyl]acetamide | |
| N-cyclohexyl-2-[4-hydroxy-1-(4-oxo-4-phenylbutyl)-4-piperidyl]-N-isopropyl-isobutyric acid amide | |
| N-cyclohexyl-2-[4-hydroxy-1-(4-p-chlorophenyl-4-oxobutyl)-4-piperidyl]-N-methyl propionamide | |
| 1-{2-[4-hydroxy-1-(4-oxo-4-phenylbutyl)-4-piperidyl]-2-methylpropionyl}-4-methylpiperazine | |
| 1-{2-[4-hydroxy-1-(4-oxo-4-phenylbutyl)-4-piperidyl]- | |

| Compound | Observations, physical constants |
|---|---|
| 2-methylpropionyl}morpholine | |
| 1-{2-[4-hydroxy-1-(4-oxo-4-phenylbutyl)-4-piperidyl]-<br>2-methylpropionyl}thiomorpholine | |
| 2-[4-hydroxy-1-(4-oxo-4-phenylbutyl)-4-piperidyl]-<br>2-cyclohexyl-N,N-dimethylacetamide | |
| 2-[1-(4-p-methoxyphenyl-4-oxobutyl)-4-hydroxy-<br>4-piperidyl]-N-benzyl-N-methyl propionamide | |
| 1-[4-hydroxy-1-(4-oxo-4-phenylbutyl)-4-piperidyl]-<br>1-cyclohexane-carboxylic acid N,N-dimethylamide | |
| 2-[1-(4-p-fluorophenyl-4-oxobutyl)-4-hydroxy-4-piperidyl]-<br>N-isopropyl-N-methyl-2-p-methoxyphenylacetamide | |
| 2-[1-(4-p-fluorophenyl-4-oxobutyl)-4-hydroxy-4-piperidyl]-<br>2-p-fluorophenyl-N,N-dimethyl acetamide | |
| 2-[1-(4-p-fluorophenyl-4-oxobutyl)-4-hydroxy-4-piperidyl]-<br>N,N-dimethyl-2-m-tolyl-acetamide | |

EXAMPLE 6:
2-(4-hydroxy-1-phenethyl-4-piperidyl)-N,N-dimethyl propionamide [process variant (a)]

2-(4-hydroxy-4-piperidyl)propionic acid N,N-dimethylamide and phenethyl bromide are reacted in a manner analogous to that described in Example 3. The resulting crude title compound is dissolved in ethanol, the calculated amount of fumaric acid is added and subsequently ether is added until the solution becomes turbid.

The resulting hydrogen fumarate form of the title compound has a M.P. of 188°–189° after recrystallization from ethanol/ether.

The following compounds may also be obtained in a manner analogous to that described in Example 6, by reacting the corresponding (4-hydroxy-4-piperidyl)carboxylic acid amides, produced in a manner analogous to Example 4(a) and (b), with the corresponding β-halogen-phenethyl derivatives:

| Compound | Observations, physical constants |
|---|---|
| 2-(1-o-chlorophenethyl-4-hydroxy-4-piperidyl)-<br>N-butylpropionamide | M.P. (hydrogen maleate)<br>132°–133° (from acetone/ether) |
| 2-(1-o-chlorophenethyl-4-hydroxy-4-piperidyl)-<br>N-m-tolyl-N-methyl propionamide | |
| 2-(1-m-chlorophenethyl-4-hydroxy-4-piperidyl)-<br>N-cyclohexyl-N-isopropyl propionamide | |
| 1-[2-(1-o-chlorophenethyl-4-hydroxy-4-piperidyl)-<br>propionyl]thiomorpholine | |
| 2-(1-o-chlorophenethyl-4-hydroxy-4-piperidyl)-<br>N,N-dibutyl-2-cyclohexyl-acetamide | M.P. of the hydrogen fumarate form:<br>159.5°–160.5° (from ethanol) |
| 2-(1-o-chlorophenethyl-4-hydroxy-4-piperidyl)-<br>N,N-dibutyl-propionamide | M.P. of the hydrogen maleate form:<br>140°–141.5° (from acetone/ether) |
| 2-(1-o-chlorophenethyl-4-hydroxy-4-piperidyl)-<br>N-cyclohexyl-N-methylpropionic acid amide | M.P. of the hydrogen maleate form:<br>121°–123° (from acetone) |
| 2-(1-o-chlorophenethyl-4-hydroxy-4-piperidyl)-<br>N,N-dimethyl propionamide | M.P. of the hydrogen fumarate form:<br>156°–158° (from ethanol/ether) |
| 2-(4-hydroxy-1-phenethyl-4-piperidyl)-<br>N,N-dimethyl-2-cyclohexyl-acetamide | M.P. of the hydrobromide form:<br>218°–219° (from ethanol/ether) |
| 2-(1-o-chlorophenethyl-4-hydroxy-4-piperidyl)-<br>N,N-dimethyl-2-cyclohexyl-acetamide | M.P. of the hydrobromide form:<br>203.5°–205° (from ethanol) |
| 2-(1-o-chlorophenethyl-4-hydroxy-4-piperidyl)-<br>N-methyl-N-phenyl propionamide | M.P. of the hydrogen maleate form:<br>170.5°–171.5° (from ethanol) |
| 2-(1-o-fluorophenethyl-4-hydroxy-4-piperidyl)-<br>N-cyclohexyl-N-methyl propionamide | |
| 1-[2-(1-o-chlorophenethyl-4-hydroxy-4-piperidyl)-<br>propionyl]-4-methylpiperazine | M.P. of the dihydrochloride form:<br>283°–284° (from ethanol) |
| 2-(1-o-chlorophenethyl-4-hydroxy-4-piperidyl)-<br>isobutyric acid N,N-dimethylamide | M.P. (hydrogen fumarate)<br>196°–197° C. |
| 1-[2-(1-o-chlorophenethyl-4-hydroxy-4-piperidyl)-<br>2-methylpropionyl]piperidine | M.P. 132°–133° (from acetone) |
| 1-[2-(1-o-chlorophenethyl-4-hydroxy-4-piperidyl)-<br>propionyl]morpholine | |
| 2-(1-o-chlorophenethyl-4-hydroxy-4-piperidyl)-<br>N-methyl-N-phenyl-2-m-tolyl-acetamide | |
| 2-(1-o-chlorophenethyl-4-hydroxy-4-piperidyl)-<br>N-p-fluorophenyl-N-methylpropionamide | |
| N-benzyl-2-(1-o-chlorophenethyl-4-hydroxy-<br>4-piperidyl)-3-cyclohexyl-N-methylpropionamide | |
| 2-(1-o-chlorophenethyl-4-hydroxy-4-piperidyl)-<br>2-p-chlorophenyl-N,N-dimethylacetamide | |
| 1-(1-o-chlorophenethyl-4-hydroxy-4-piperidyl)-<br>N-cyclohexyl-N-methyl-1-cyclohexane-carboxylic acid amide | |
| 2-(1-o-chlorophenethyl-4-hydroxy-4-piperidyl)-<br>N-cyclohexyl-2-p-methoxyphenyl-N-methylacetamide | M.P. (hydrochloride) 238°–239°<br>(from acetone/ether) |
| 2-(1-o-chlorophenethyl-4-hydroxy-4-piperidyl)-<br>N-cyclohexyl-N-methyl isobutyric acid amide | |
| 2-(1-o-chlorophenethyl-4-hydroxy-4-piperidyl)-<br>N-cyclohexyl-N-isopropyl propionamide | |

-continued

| Compound | Observations, physical constants |
|---|---|
| 2-(1-o-chlorophenethyl-4-hydroxy-4-piperidyl)-N-isopropyl-N-methyl propionamide | |
| 2-(1-o-chlorophenethyl-4-hydroxy-4-piperidyl)-N-cyclohexyl-2-p-fluorophenyl-N-methylacetamide | |
| N-cyclohexyl-2-(1-m-methylphenethyl-4-hydroxy-4-piperidyl)-N-methyl propionamide | |
| 2-(1-o-chlorophenethyl-4-hydroxy-4-piperidyl)-N-cyclohexyl-2-phenyl-N-methylacetamide | |
| 2-(4-hydroxy-1-o-methoxyphenethyl-4-piperidyl)-N-cyclohexyl-N-methyl propionamide | |
| 2-(1-o-chlorophenethyl-4-hydroxy-4-piperidyl)-N-phenyl isobutyric acid amide | |
| 2-(1-o-chlorophenethyl-4-hydroxy-4-piperidyl)-N-p-chlorophenyl propionamide | |
| 2-(1-o-chlorophenethyl-4-hydroxy-4-piperidyl)-N-p-tolyl-propionamide | |
| 2-(1-o-chlorophenethyl-4-hydroxy-4-piperidyl)-N-m-methoxyphenyl propionamide | |
| 2-(1-o-chlorophenethyl-4-hydroxy-4-piperidyl)-N-phenyl propionamide | M.P. of the hydrogen fumarate form: 159°–161° (from ethanol) |
| 2-(1-o-chlorophenethyl-4-hydroxy-4-piperidyl)-propionamide | M.P. of the hydrogen maleate form: 219°–221° (from acetone) |
| 2-cyclohexyl-2-(4-hydroxy-1-m-methylphenethyl-4-piperidyl)-n-p-fluorophenylacetamide | |
| 2-p-chlorophenyl-2-(4-hydroxy-1-o-methoxyphenethyl-4-piperidyl)-N-phenylacetamide | |
| 2-(4-hydroxy-1-phenethyl-4-piperidyl)-N-phenyl propionamide | |
| 2-(1-o-chlorophenethyl-4-hydroxy-4-piperidyl)-3-cyclohexyl-N,N-dimethylpropionic amide | M.P. (hydrogen fumarate) 134°–136° (from acetone) |

EXAMPLE 7:
2-(4-hydroxy-1-phenethyl-4-piperidyl)propionic acid ethyl ester [process variant (b)]

A solution of 6.4 g of propionic acid ethyl ester in 25 cc of anhydrous tetrahydrofuran is added dropwise at −75° to a solution of N,N-diisopropyllithium amide (produced from 8.9 cc of diisopropylamine in 60 cc of anhydrous tetrahydrofuran and 25 cc of a 20% n-butyl-lithium solution in hexane at a temperature of −75°). After stirring at the same temperature for one hour, a solution of 12.5 g of 1-phenethyl-4-piperidone in 50 cc of tetrahydrofuran is added within 20 minutes and the mixture is allowed to react at about −70° for a further 2 hours. The reaction temperature is then allowed to rise to about −10° and the reaction mixture is decomposed with 100 cc of water. After extracting repeatedly with ether, the crude product is isolated by concentrating the extracts which have been dried over magnesium sulphate. The resulting red-coloured oil is dissolved in acetone, the calculated amount of maleic acid is added and the resulting crude crystalline product is recrystallized repeatedly from acetone. The hydrogen maleate form of the title compound, having a M.P. of 138°–139°, is obtained.

The compounds described in Example 3 may also be obtained in a manner analogous to that described in Example 7, by reacting the corresponding 1-phenethyl-4-piperidone derivatives with the corresponding carboxylic acid esters. Also are obtained 2-(1-o-chlorophenethyl)-4-hydroxy-4-piperidyl)-3-butenacid ethyl ester, M.P. (hydrogen fumarate) 181°–183° [from ethanol (ether)] 2-(1-o-chloro-phenethyl-4-hydroxy-4-piperidyl)-4-methyl-3-pentenacid ethyl ester.

EXAMPLE 8:
2-(4-hydroxy-1-phenethyl-4-piperidyl)-N,N-dimethyl propionamide

A solution of 5.05 g of N,N-dimethylpropionic acid amide in 25 cc of anhydrous tetrahydrofuran is added dropwise, while stirring, to a solution of N,N-diisopropyl-lithium amide (produced from 8.9 cc of diisopropylamine in 75 cc of anhydrous tetrahydrofuran and 25 cc of a 20% n-butyl-lithium solution in hexane at a temperature of −75°). The reaction mixture is stirred at −75° for one hour, and a solution of 10.2 g of 1-phenethyl-4-piperidone in 30 cc of anhydrous tetrahydrofuran is then added dropwise at the same temperature. After a reaction time of one hour at −75°, the temperature is allowed to rise to about −10° and the reaction mixture is then decomposed with 50 cc of a 20% potassium carbonate solution. Extraction is repeatedly effected with ether, the dried extracts are concentrated by evaporation and the semi-crystalline crude base is dissolved in ethanol. After the addition of an equivalent amount of fumaric acid, ether is added until the solution becomes turbid and the resulting crude crystalline product is purified by recrystallizing again from ethanol. The hydrogen fumarate form of the title compound, having a M.P. of 188°–189°, is obtained.

The following compounds may also be obtained in a manner analogous to that described in Example 8, by reacting the corresponding 1-phenethyl-4-piperidone derivatives with the corresponding carboxylic acid amides:

| Compound | Observations, physical constants |
|---|---|
| 2-(1-o-chlorophenethyl-4-hydroxy-4-piperidyl)-N-p-chlorophenyl-N-methylbutenic acid amide | |
| 2-(1-o-chlorophenethyl-4-hydroxy-4-piperidyl)-N-m-tolyl-N-methylpropionamide | |

| Compound | Observations, physical constants |
|---|---|
| 2-(1-m-chlorophenethyl-4-hydroxy-4-piperidyl)-N-cyclohexyl-N-isopropyl propionamide | |
| 1-[2-(1-o-chlorophenethyl-4-hydroxy-4-piperidyl)-propionyl]thiomorpholine | |
| 2-(1-o-chlorophenethyl-4-hydroxy-4-piperidyl)-N,N-dibutyl-2-cyclohexyl-acetamide | M.P. of the hydrogen fumarate form: 159.5°–160.5° (from ethanol) |
| 2-(1-o-chlorophenethyl-4-hydroxy-4-piperidyl)-N,N-dibutyl-propionamide | M.P. of the hydrogen maleate form: 140°–141.5° (from acetone/ether) |
| 2-(1-o-chlorophenethyl-4-hydroxy-4-piperidyl)-N-cyclohexyl-N-methylpropionic acid amide | M.P. of the hydrogen maleate form: 121°–123° (from acetone) |
| 2-(1-o-chlorophenethyl-4-hydroxy-4-piperidyl)-N,N-dimethyl propionamide | M.P. of the hydrogen fumarate form: 156°–158° (from ethanol/ether) |
| 2-(4-hydroxy-1-phenethyl-4-piperidyl)-N,N-dimethyl-2-cyclohexyl-acetamide | M.P. of the hydrobromide form: 218°–219° (from ethanol/ether) |
| 2-(1-o-chlorophenethyl-4-hydroxy-4-piperidyl)-N,N-dimethyl-2-cyclohexyl-acetamide | M.P. of the hydrobromide form: 203.5°–205° (from ethanol) |
| 2-(1-o-chlorophenethyl-4-hydroxy-4-piperidyl)-N-methyl-N-phenyl propionamide | M.P. of the hydrogen maleate form: 170.5°–171.5° (from ethanol) |
| 2-(1-o-fluorophenethyl-4-hydroxy-4-piperidyl-N-cyclohexyl-N-methyl propionamide | |
| 1-[2-(1-o-chlorophenethyl-4-hydroxy-4-piperidyl)-propionly]-4-methylpiperazine | M.P. of the dihydrochloride form: 283°–284° (from ethanol) |
| 2-(1-o-chlorophenethyl-4-hydroxy-4-piperidyl)-isobutyric acid N,N-dimethylamide | M.P. (hydrogen fumarate) 196°–197° |
| 1-[2-(1-o-chlorophenethyl-4-hydroxy-4-piperidyl)-2-methylpropionyl]piperidine | M.P. 132°–133° (from acetone) |
| 1-[2-(1-o-chlorophenethyl-4-hydroxy-4-piperidyl)-propionyl]morpholine | |
| 2-(1-o-chlorophenethyl-4-hydroxy-4-piperidyl)-N-methyl-N-phenyl-2-m-tolyl-acetamide | |
| 2-(1-o-chlorophenethyl-4-hydroxy-4-piperidyl)-N-p-fluorophenyl-N-methyl propionamide | |
| N-benzyl-2-(1-o-chlorophenethyl-4-hydroxy-4-piperidyl)-3-cyclohexyl-N-methyl propionamide | |
| 2-(1-o-chlorophenethyl-4-hydroxy-4-piperidyl)-2-p-chlorophenyl-N,N-dimethylacetamide | |
| 1-(1-o-chlorophenethyl-4-hydroxy-4-piperidyl)-N-cyclohexyl-N-methyl-1-cyclohexanecarboxylic acid amide | |
| 2-(1-o-chlorophenethyl-4-hydroxy-4-piperidyl)-N-cyclohexyl-2-p-methoxyphenyl-N-methylacetamide | M.P. (hydrochloride) 238°–239° (from ethanol/ether) |
| 2-(1-o-chlorophenethyl-4-hydroxy-4-piperidyl)-N-cyclohexyl-N-methyl isobutyric acid amide | |
| 2-(1-o-chlorophenethyl-4-hydroxy-4-piperidyl)-N-cyclohexyl-N-isopropyl propionamide | |
| 2-(1-o-chlorophenethyl-4-hydroxy-4-piperidyl)-N-isopropyl-N-methyl propionamide | |
| 2-(1-o-chlorophenethyl-4-hydroxy-4-piperidyl)-N-cyclohexyl-2-p-fluorophenyl-N-methylacetamide | |
| N-cyclohexyl-2-(1-m-methylphenethyl-4-hydroxy-4-piperidyl)-N-methyl propionamide | |
| 2-(1-o-chlorophenethyl-4-hydroxy-4-piperidyl)-N-cyclohexyl-2-phenyl-N-methylacetamide | |
| 2-(4-hydroxy-1-o-methoxyphenethyl-4-piperidyl)-N-cyclohexyl-N-methyl propionamide | |
| 2-(1-o-chlorophenethyl-4-hydroxy-4-piperidyl)-3-cyclohexyl-N,N-dimethylpropionic acid amide | M.P. (hydrogen fumarate) 134°–136° (from acetone) |
| 2-(1-o-chlorophenethyl-4-hydroxy-4-piperidyl)-N-butylpropionamide | M.P. (hydrogen maleate) 132°–133° (from acetone/ether) |

EXAMPLE 9:
2-(1-o-chlorophenethyl-4-hydroxy-4-piperidyl)-N-phenylpropionamide 48 cc of n-butyl-lithium in hexane are added dropwise at 0°, in an atmosphere of nitrogen with stirring, to a solution of 9 g of N-phenylpropionamide in 90 cc of anhydrous tetrahydrofuran. The mixture is stirred at 45°–48° for 2½ hours and a solution of 10.5 g of N-o-chlorophenethyl-4-piperidone in 25 cc of anhydrous tetrahydrofuran is added dropwise within 50 minutes. The heating (oil bath) is removed and the reaction mixture is stirred for a further hour while cooling slowly. 10 cc of a 20% potassium carbonate solution are subsequently added to the reaction solution while stirring and cooling with ice, dilution is effected with ether and the organic phase is decanted, dried over magnesium sulphate and concentrated by evaporation at reduced pressure. The resulting crude compound is filtered over silica gel (eluant: chloroform containing 3% of methanol) and an equivalent amount of fumaric acid is added to the resulting title compound in ethanol whereby this crystallizes as hydrogen fumarate. The hydrogen fumarate form of the title compound has a M.P. of 159°–161°.

The following conpounds may be obtained in a manner analogous to that described in Example 9, by reacting the corresponding 1-phenethyl-4-piperidone derivatives with the corresponding N-phenylcarboxylic acid amides:

| Compound | Observations, physical constants |
|---|---|
| 2-(1-o-chlorophenethyl-4-hydroxy-4-piperidyl)-<br>N-phenyl isobutyric acid amide | |
| 2-(1-o-chlorophenethyl-4-hydroxy-4-piperidyl)-<br>N-p-chlorophenyl propionamide | |
| 2-(1-o-chlorophenethyl-4-hydroxy-4-piperidyl)-<br>N-p-tolyl-propionamide | |
| 2-(1-o-chlorophenethyl-4-hydroxy-4-piperidyl)-<br>N-m-methoxyphenyl propionamide | |
| 2-(1-o-fluorophenethyl-4-hydroxy-4-piperidyl)-<br>2-phenyl-N-phenylacetamide | |
| 2-cyclohexyl-2-(4-hydroxy-1-m-methylphenethyl-<br>4-piperidyl)-N-p-fluorophenyl acetamide | |
| 2-p-chlorophenyl-2-(4-hydroxy-1-o-methoxyphenethyl-<br>4-piperidyl)-N-phenylacetamide | |
| 2-(4-hydroxy-1-phenethyl-4-piperidyl)-<br>N-phenyl propionamide | |

EXAMPLE 10:
2-(1-o-chlorophenethyl-4-hydroxy-4-piperidyl)propionamide [process variant (d)]

20 cc of a 40% hydrogen peroxide solution are added dropwise within 15 minutes, while stirring and cooling with ice, to a solution of 17.5 g of 2-(1-o-chlorophenethyl-4-hydroxy-4-piperidyl)propionitrile in 100 cc of 95% ethanol and 20 cc of 3 N caustic soda solution. The mixture is then allowed to stand at room temperature for 18 hours and the ethanol is subsequently evaporated at reduced pressure. 100 cc of a 4.4 N sodium bisulphite solution are slowly added to the aqueous phase while cooling strongly with ice and stirring, the reaction mixture is allowed to stand at 20° for 20 hours and is made alkaline with an excess of 5 N caustic soda solution. Extraction is effected several times with chloroform; the organic phase is washed with water, dried over magnesium sulphate and concentrated by evaporation at reduced pressure. The resulting crude title compound crystallizes from acetone and has a M.P. of 141°–142°. The corresponding hydrogen maleate form of the title compound has a M.P. of 219°–221°.

The starting material may be obtained as follows:

(a) 48 cc of n-butyl-lithium in hexane are added dropwise at 0°, in an atmosphere of nitrogen and with stirring, to a solution of 17 cc of diisopropylamine in 250 cc of anhydrous tetrahydrofuran. The mixture is stirred at 0° for a further 15 minutes, is cooled to −70°, and 4.2 cc of propionitrile in 10 cc of anhydrous tetrahydrofuran are added dropwise while stirring. The reaction mixture is stirred at −70° for one hour and subsequently a solution of 14.2 g of o-chlorophenethylpiperidin-4-one in 25 cc of anhydrous tetrahydrofuran is added dropwise and the mixture is stirred at −70° for a further hour. The temperature is raised to 0°, 5 cc of a 20% potassium carbonate solution are added to the reaction mixture and the organic phase is decanted. The residue is washed twice with ether, the combined solvent phases are dried over magnesium sulphate and concentrated by evaporation at reduced pressure. Fumaric acid is added to the resulting 2-(1-o-chlorophenethyl-4-hydroxy-4-piperidyl)propionitrile in acetone and the fumarate is crystallized with the addition of ether. The fumarate has a M.P. of 187°–189°.

The following (4-hydroxy-4-piperidyl)carboxylic acid amide derivatives may also be obtained in a manner analogous to that described in Example 10, by hydrolysis of the corresponding nitriles produced in accordance with Example 10(a):

2-(4-hydroxy-1-phenethyl-4-piperidyl)isobutyric acid amide,
2-(1-o-chlorophenethyl-4-hydroxy-4-piperidyl)butenic acid amide,
2-[1-(4-p-fluorophenyl-4-oxobutyl)-4-hydroxy-4-piperidyl]propionic acid amide,
2-[4-hydroxy-1-(4-oxo-4-phenylbutyl)-4-piperidyl]propionic acid amide,
2-[4-hydroxy-1-(4-oxo-4-phenylbutyl)-4-piperidyl]-2-phenylacetamide,
2-cyclohexyl-2-[1-(4-p-fluorophenyl-4-oxobutyl)-4-hydroxy-4-piperidyl]acetamide.

EXAMPLE 11:
2-(1-o-chlorophenethyl-4-hydroxy-4-piperidyl)-N-butylpropionamide [process variant (e)]

A solution of 5 g of 2-(1-o-chlorophenethyl-4-hydroxy-4-piperidyl)propionic acid phenyl ester and 50 cc of n-butylamine is boiled at reflux for 18 hours in an atmosphere of nitrogen. The excess n-butylamine is then removed by evaporation at reduced pressure, the residue is taken up in chloroform and the organic phase is washed twice with water and dried over magnesium sulphate. The chloroform is evaporated at reduced pressure. The residue is treated with maleic acid in acetone and the title compound is crystallized from acetone/ether (M.P. of hydrogen maleate 132°–133° C.).

The amide compounds described in Examples 4–7 may also be obtained in a manner analogous to that described in Example 11, by reacting the corresponding (4-hydroxy-4-piperidyl)carboxylic acid phenyl ester derivatives with the corresponding amines.

EXAMPLE 12: Galenic preparations (a) Capsules

Composition:

| 2-[4-hydroxy-1-(4-oxo-4-phenylbutyl)-<br>4-piperidyl]propionic acid ethyl<br>ester hydrochloride | 20 mg |
|---|---|
| mannitol | 200 mg |
| microcrystalline cellulose | 75 mg |
| talc | 15 mg |
| yields one capsule of | 310 mg |

(b) Tablets

Composition:

| 2-[4-hydroxy-1-(4-oxo-4-phenylbutyl)-4-piperidyl]propionic acid ethyl ester hydrochloric | 10 mg/dose |
| --- | --- |
| lactose | 255 mg/dose |
| maize starch | 33 mg/dose |
| polyvinyl pyrrolidone (Kollidon 30) | 20 mg/dose |
| magnesium stearate | 2 mg/dose |

The active agent is mixed with the lactose and the maize starch and is worked up with the remaining components in accordance with known tabletting techniques into tablets of 320 mg.

The compounds of formula I are useful because they possess pharmacological activity in animals. In particular, the compounds of formula I are useful as analgesic agents for the treatment of pains in animals as indicated in standard tests, for example on the tail flick test in mice on s.c. administration of from about 1 to about 30 mg/kg animal body weight of the compounds, and in the phenylbenzoquinone syndrome test in mice on p.o. administration of from about 1.5 to about 30 mg/kg animal body weight.

For the above mentioned use the dosage will, of course, vary depending on the compound employed, mode of administration and therapy desired. However, in general, satisfactory results are obtained when administered at a daily dosage of from 1 mg to about 30 mg per kg animal body weight, conveniently given in divided doses 2 to 4 times a day or in sustained release form. For the larger mammal, the total daily dosage is in the range from about 50 to about 500 mg, and dosage forms suitable for oral administration comprise from about 10 mg to about 250 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

Preferred compositions are those having $R_2$ ethoxy, $R_3$ phenyl, substituted phenyl or alkyl and $R_4$ hydrogen.

In one group of compounds $R_1$ is phenethyl or substituted phenethyl.

In another group of compounds $R_1$ is butyrophenone or substituted butyrophenone.

Further groups are $R_3$ is alkyl, cycloalkyl or cycloalkylalkyl and $R_4$ is (i) hydrogen or lower alkyl or (ii) hydrogen or (iii) $R_3$ and $R_4$ form a cycloalkyl ring together with the carbon atom to which they are bound.

Further groups are $R_2$ is (i) alkoxy or (ii)

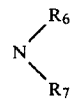

wherein $R_6$ and $R_7$ are as defined above provided that $R_6$ and $R_7$ are other than hydrogen.

In another group of compounds $R_2$ is other than alkoxy when $R_3$ is alkyl or phenyl or substituted phenyl and $R_4$ is hydrogen.

EXAMPLE 13

The following compounds may be prepared in manner analogous to that described in Example 8 but employing appropriate starting materials in approximately equivalent amounts.

| Compound | Observations, physical constants |
| --- | --- |
| 2-(1-o-chlorophenethyl-4-hydroxy-4-piperidyl)-N-cyclohexyl-propionamide | M.P. 110°–111° |
| 2-(1-o-chlorophenethyl-4-hydroxy-4-piperidyl)-N-cyclopentyl-N-methylpropionamide | M.P. (hydrobromide) 167°–169° |
| 2-(1-o-chlorophenethyl-4-hydroxy-4-piperidyl)-N,N-dicyclohexylpropionamide | M.P. (hydrogenmaleate) 155°–158° |
| N-cyclohexyl-N-methyl-2-(1-phenethyl-4-hydroxy-4-piperidyl)propionic acid amide | M.P. (hydrochloride) 215°–217° |
| 2-(1-o-chlorophenethyl-4-hydroxy-4-piperidyl)-N,N-diisopropylpropionamide | M.P. (hydrobromide) 202°–204° |
| N-tert.-butyl-2-(1-o-chlorophenethyl-4-hydroxy-4-piperidyl)-N-cyclohexylpropionamide | M.P. (hydrochloride) 174°–175° |
| 2-(1-p-bromophenethyl-4-hydroxy-4-piperidyl)-N-cyclohexyl-N-methylpropionamide | M.P. (hydrochloride) 221°–223° |
| 2-(o-chlorophenethyl-4-hydroxy-4-piperidyl)-N-cyclohexyl-N-methylpropionamide | M.P. (hydrochloride) 176°–177° |

| Compound | Observations, physical constants |
|---|---|
| N-cyclohexyl-2-(1-p-methylphenethyl-4-hydroxy-4-piperidyl)-N-methylpropionamide. | M.P. (hydrochloride) 215°–217° |
| 2-(1-o-chlorophenethyl-4-hydroxy-4-piperidyl)-N-cyclohexyl-N-methylcyclopropionic acid amide | M.P. (hydrogenfumarate) 228°–229° |
| 2-(1-o-chlorophenethyl-4-hydroxy-4-piperidyl)-N,N-diisopropyl isobutyric acid amide | M.P. 143°–144° |
| N-cyclohexyl-N-methyl-2-(1-o-methoxyphenethyl)-4-hydroxy-4-piperidyl isobutyric acid amide | M.P. (hydrochloride) 210°–211° |
| 2-(1-o-chlorophenethyl-4-hydroxy-4-piperidyl)-N-cyclohexyl-N-methyl isovaleric acid amide | M.P. (hydrobromide) 118°–124° |
| 2-(1-o-chlorophenethyl-4-hydroxy-4-piperidyl)-N-cyclohexyl-N-methyl caproic acid amide | M.P. (hydrogenfumarate) 165°–167° |
| 2-(1-o-chlorophenethyl-4-hydroxy-4-piperidyl)-N-cyclohexyl-N-methyl-cyclopentane-carboxylic acid | M.P. (fumarate) 215°–217° |
| 2-(1-o-chlorophenethyl-4-hydroxy-4-piperidyl)-N-cyclohexyl-N-methyl butyric acid amide | M.P. (hydrogenfumarate) 185°–187° |

Furthermore, the compounds of formula I are useful as agents for the treatment and prophylaxis of migraine, as indicated by standard tests, for example, as observed in the inhibition of serotonin toxicity in the serotonin toxicity test in guinea-pigs in orally administered doses of from about 0.001 to about 1.0 mg/kg animal body weight.

The dosage will, of course, vary depending on the compound employed and the mode of administration and the therapy desired. However, in general, satisfactory results are obtained when administered at a daily dosage of from about 0.0001 to about 1.0 mg/kg bodyweight, conveniently given in divided doses 2 to 4 times a day or in sustained release form. For the larger mammal, the total daily dosage is in the range from about 1 to 10 mg, and dosage forms suitable for oral administration comprise from about 0.25 to 5 mg of the compounds admixed with a solid or liquid pharmaceutical carrier or diluent.

Additionally, the compounds possess antidepressant characteristics similar to those of Mianserin as indicated in standard tests in animals, for example in the antagonism of the central effects of L-5-HTP (L-5-HT) in rats. The compounds are administered i.p. at from about 0.3 to about 60 mg/kg of animal body weight.

The dosage will, of course, vary depending on the compound employed, the mode of administration and the therapy desired. However, in general, satisfactory results are obtained when administered at a daily dosage of from about 0.3 to about 60 mg/kg of animal bodyweight, conveniently given in divided doses 2 to 4 times a day or in sustained release form. For the larger mammal, the total daily dosage is in the range from about 5 to about 150 mg, and dosage forms suitable for oral administration comprise from about 1 to about 75 mg of the compounds admixed with a solid or liquid pharmaceutical carrier or diluent.

What is claimed is:

1. A compound of the formula,

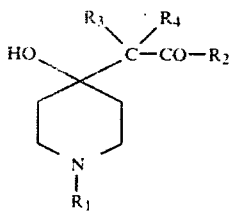

wherein $R_1$ is butyrophenone or butyrophenone mono-substituted in the phenyl ring by fluorine, chlorine, bromine, lower alkyl or lower alkoxy, $R_2$ is an

group, wherein independently each of $R_6$ and $R_7$ is hydrogen, lower alkyl or cycloalkyl, phenyl, phenyl monosubstituted by fluorine, chlorine, bromine, lower alkyl or lower alkoxy, lower phenylalkyl or lower phenylalkyl monosubstituted in the phenyl ring by fluorine, chlorine, bromine, lower alkyl or lower alkoxy, $R_3$ is lower alkyl or cycloalkyl, phenyl or phenyl monosubstituted by fluorine, chlorine, bromine, lower alkyl or lower alkoxy, and $R_4$ is hydrogen or lower alkyl, or a pharmaceutically acceptable acid addition salt thereof.

2. A compound of claim 1 wherein $R_3$ is alkyl or cycloalkyl.

3. A compound of claim 2, wherein $R_4$ is hydrogen.

4. A compound of claim 1, wherein $R_2$ is

wherein $R_6$ and $R_7$ are both other than hydrogen.

5. A compound of claim 1 where $R_6$ and $R_7$ are lower alkyl or cycloalkyl.

6. A compound of claim 1 where $R_3$ represents lower alkyl.

7. A compound of claim 1 where $R_4$ epresents hydrogen.

8. A compound of claim 1 where $R_1$ is butyrophenone or p-fluorobutyrophenone, $R_2$ is $NR_6R_7$ where $R_6$ is lower alkyl or cycloalkyl and $R_7$ is lower alkyl, or $R_6$ is hydrogen and $R_7$ is phenyl or said monosubstituted phenyl, $R_3$ is lower alkyl and $R_4$ is hydrogen or lower alkyl.

9. A compound of claim 1 wherein $R_2$ is dimethylamine or N-cyclohexyl-N-methylamine.

10. A compound of claim 1 which is 2-[4-hydroxy-1(4-oxo-4-phenylbutyl)-4-piperidyl]-N,N-dimethyl propionamide.

11. A compound of claim 1 which is 2-[1-(4-p-fluorophenyl-4-oxobutyl)-4-hydroxy-4-piperidyl]-N-phenylpropionamide.

12. A compound of claim 1 which is 2-[4-hydroxy-1-(4-oxo-4-phenylbutyl)-4-piperidyl]-N-cyclohexyl-N-methyl propionamide.

13. A compound of claim 1 which is 2-[1-(4-fluorophenyl-4-oxobutyl)-4-hydroxy-4-piperidyl]-N,N-dimethyl propionamide.

14. A compound of claim 1 which is 2-[4-hydroxy-1-(4-oxo-4-phenylbutyl)-4-piperidyl]-N-methyl-N-phenyl propionamide.

15. A compound of claim 1 which is 2-[1-(4-p-fluorophenyl-4-oxobutyl)-4-hydroxy-4-piperidyl]-methyl-N-phenyl propionamide.

16. A compound of claim 1 which is 2-[1-(4-p-fluorophenyl-4-oxobutyl)-4-hydroxy-4-piperidyl]-N,N-dimethylisobutyric acid amide.

17. A pharmaceutical composition comprising an anti-depressant effective amount of a compound of claim 1 in association with a pharmaceutical carrier or diluent.

18. A method of treating pain and migraine in animals which comprises administering a therapeutically effective amount of a compound of claim 1 to an animal in need of such treatment.

19. A method of treating depressions in animals which comprises administering a therapeutically effective amount of a compound of claim 1 to an animal in need of such treatment.

* * * * *